(12) United States Patent
Steghöfer et al.

(10) Patent No.: US 10,694,949 B2
(45) Date of Patent: Jun. 30, 2020

(54) COMPUTER IMPLEMENTED METHOD FOR CALCULATING VALUES INDICATIVE FOR THE LOCAL SPATIAL STRUCTURE OF CONDUCTING PROPERTIES OF HEART MUSCLE TISSUE AND COMPUTER PROGRAMS THEREOF

(71) Applicants: GALGO MEDICAL, SL, Barcelona (ES); HOSPITAL CLÍNIC DE BARCELONA, Barcelona (ES)

(72) Inventors: Martin Steghöfer, Barcelona (ES); Luis Serra Del Molino, Barcelona (ES); Javier Planes Cid, Lleida (ES); Antonio Berruezo Sánchez, Barcelona (ES)

(73) Assignees: GALGO MEDICAL, SL, Barcelona (ES); HOSPITAL CLÍNIC DE BARCELONA, Barcelona (ES)

( * ) Notice: Subject to any disclaimer, the term of this patent is extended or adjusted under 35 U.S.C. 154(b) by 100 days.

(21) Appl. No.: 16/052,905

(22) Filed: Aug. 2, 2018

(65) Prior Publication Data

US 2019/0046040 A1  Feb. 14, 2019

(30) Foreign Application Priority Data

Aug. 8, 2017 (EP) .................................. 17382559

(51) Int. Cl.
*G06K 9/00* (2006.01)
*A61B 5/00* (2006.01)
(Continued)

(52) U.S. Cl.
CPC .......... *A61B 5/0044* (2013.01); *G06K 9/3233* (2013.01); *G06T 7/0012* (2013.01);
(Continued)

(58) Field of Classification Search
CPC ....... A61B 5/0044; A61B 5/042; A61B 5/055; A61B 5/7264; G06K 9/3233; G06T 15/06;
(Continued)

(56) References Cited

U.S. PATENT DOCUMENTS 9,875,537 B2 * 1/2018 Barbarito .............. G06T 7/0012
10,304,185 B2 * 5/2019 Steghofer ............. G06T 7/0012
(Continued)

FOREIGN PATENT DOCUMENTS

EP   2672889   12/2013
EP   2755185   7/2014
(Continued)

OTHER PUBLICATIONS

J. M. Cook, "Technical Notes and Short Papers: Rational Formulae for the Production of a Spherically Symmetric Probability Distribution," Mathematical Tables and Other Aids to Computation, vol. 11, pp. 81-82, 1957.
(Continued)

*Primary Examiner* — Charles T Shedrick
(74) *Attorney, Agent, or Firm* — Silvia Salvadori

(57) ABSTRACT

A method for calculating values indicative for the local spatial structure of conducting properties of heart muscle tissue. The method uses a continuous ROI where there may exist a CC, each point of the ROI being associated with a value of a given spatial distribution. The method for each one of the points: spans rays within the ROI in multiple 3-D directions using coordinates of a reference coordinate system of each point, providing a structure with a plurality of rays with a given geometry; defines a sequence of sampling points on each ray of said structure; maps the value of the spatial distribution on each defined sampling point of each ray of the structure; classifies each ray of the structure by
(Continued)

assigning a single value, providing an associated ray value; and reduces each structure to a single point value in view of said geometry and their associated ray value.

17 Claims, 3 Drawing Sheets

(51) Int. Cl.
| | | |
|---|---|---|
| *G06T 7/00* | (2017.01) | |
| *G06K 9/32* | (2006.01) | |
| *G06T 15/06* | (2011.01) | |
| *G06T 15/08* | (2011.01) | |
| *A61B 5/055* | (2006.01) | |
| *A61B 5/042* | (2006.01) | |

(52) U.S. Cl.
CPC ............. *G06T 15/06* (2013.01); *G06T 15/08* (2013.01); *A61B 5/042* (2013.01); *A61B 5/055* (2013.01); *A61B 5/7264* (2013.01); *G06T 2207/10081* (2013.01); *G06T 2207/10088* (2013.01); *G06T 2207/30048* (2013.01)

(58) Field of Classification Search
CPC .......... G06T 15/08; G06T 2207/10081; G06T 2207/10088; G06T 7/0012; G06T 2207/30048
See application file for complete search history.

(56) References Cited

U.S. PATENT DOCUMENTS

| | | | | |
|---|---|---|---|---|
| 2011/0224962 | A1* | 9/2011 | Goldberger | G06T 7/0012 703/11 |
| 2014/0249790 | A1* | 9/2014 | Spilker | G16H 30/20 703/11 |
| 2017/0068796 | A1 | 3/2017 | Passerini et al. | |
| 2017/0178403 | A1 | 6/2017 | Krummen et al. | |

FOREIGN PATENT DOCUMENTS

| | | |
|---|---|---|
| EP | 2950270 | 3/2017 |
| WO | 20160014949 | 1/2016 |

OTHER PUBLICATIONS

G. Marsaglia, "Choosing a Point from the Surface of a Sphere," The Annals of Mathematical Statistics, vol. 43, No. 2, pp. 645-646, 1972.

"Sphere Point Picking," [Online]. Available: http://mathworld.wolfram.com/SpherePointPicking.html.

Priority Search Report and written opinion dated Nov. 2, 2017 for EP application No. 17382559.7.

Serra L et al: "Identification of border-zone corridors in the left ventricle using the core expansion method", Proceedings Optical Diagnostics of Living Cells 11, SPIE, US, vol. 10160, Jan. 26, 2017 (Jan. 26, 2017), pp. 1016011-1016011, XP060081653, ISSN: 0277-786X, DO!: 10.1117/12.2255817 ISBN: 978-1-5106-1354-6.

Kivanc Yalin et al: "Cardiac Magnetic Resonance for Ventricular Arrhythmia Therapies in Patients with Coronary Artery Disease Corresponding Author", Journal of Atrial Fibrillation, Jul. 2015 (Jul. 2015), XP055416348, Retrieved rom the Internet: URL:https://www.ncbi.nlm.nih.gov/pmc/artic les/PMC5135117/pdf/jafib-08-01242.pdf [retrieved on Oct. 17, 2017].

J. Fernandez-Armenta et al: "Three-Dimensional Architecture of Scar and Conducting Channels Based on High Resolution ce-CMR: Insights for Ventricular Tachycardia Ablation", Circulation: Arrhythmia and Electrophysiology,2013;6:528-537.

* cited by examiner

COMPUTER IMPLEMENTED METHOD FOR CALCULATING VALUES INDICATIVE FOR THE LOCAL SPATIAL STRUCTURE OF CONDUCTING PROPERTIES OF HEART MUSCLE TISSUE AND COMPUTER PROGRAMS THEREOF

RELATED APPLICATION

This application claims priority to European patent application no. EP 17382559.7 filed on 8 Aug. 2017, the contents of which are hereby incorporated by reference as if set forth in their entirety.

TECHNICAL FIELD

The present invention is directed, in general, to methods for characterizing heart muscle tissue. In particular, the invention relates to a computer implemented method, and computer programs thereof, for calculating values indicative for the local spatial structure of conducting properties of heart muscle tissue.

BACKGROUND OF THE INVENTION

When heart muscle tissue becomes fibrotic due to a heart attack, myocardiopathy or any other reason, it changes its electrical conducting properties. This conductivity (how diseased cells are organized in the heart, that is, the resulting topological and morphological structure of the fibrotic tissue) is important to understand arrhythmias. Having an idea of the conductivity of a patient's heart tissue in a minimally invasive way (a scan) is key to help to decide on its treatment.

Obtaining a 3D data of the heart muscle is possible using MRI, CT, echography, nuclear imaging, electroanatomical mapping, or other image acquisition technologies.

There are known some patent application in this field.

US-A1-2017178403 provides a system for computational localization of fibrillation sources. In some implementations, the system performs operations comprising generating a representation of electrical activation of a patient's heart and comparing, based on correlation, the generated representation against one or more stored representations of hearts to identify at least one matched representation of a heart. The operations can further comprise generating, based on the at least one matched representation, a computational model for the patient's heart, wherein the computational model includes an illustration of one or more fibrillation sources in the patient's heart. Additionally, the operations can comprise displaying, via a user interface, at least a portion of the computational model.

US-A1-2017068796 discloses a method and system for simulating patient-specific cardiac electrophysiology including the effect of the electrical conduction system of the heart. A patient-specific anatomical heart model is generated from cardiac image data of a patient.

The electrical conduction system of the heart of the patient is modeled by determining electrical diffusivity values of cardiac tissue based on a distance of the cardiac tissue from the endocardium. A distance field from the endocardium surface is calculated with sub-grid accuracy using a nested-level set approach. Cardiac electrophysiology for the patient is simulated using a cardiac electrophysiology model with the electrical diffusivity values determined to model the Purkinje network of the patient.

EP-A2-2672889 discloses a method of planning a patient-specific cardiac procedure including receiving three-dimensional imaging data of a patient's heart, simulating at least one of electrophysiological or electromechanical activity of at least a portion of the patient's heart using the three-dimensional imaging data, and planning the patient-specific cardiac procedure based on the simulating. The cardiac procedure is for providing a preselected alteration of at least one of electrophysiological or electromechanical behavior of the patient's heart.

EP-B1-2950270 discloses a computer implemented method for identifying channels from representative data in a 3D volume. The method comprises identifying, in a 3D volume, a zone of a first type (H) and a zone of a second type (BZ) and: automatically identifying as a candidate channel (bz) a path running through the zone of a second type (BZ) and extending between two points of the zone of a first type (H); and automatically performing, on a topological space (H_and_BZ_topo), homotopic operations between the candidate channel (bz) and paths (h) running only through the zone of a first type (H), and if the result of said homotopic operations is that the candidate channel (bz) is not homotopic to any path running only through the zone of a first type (H) identifying the candidate channel (bz) as a constrained channel.

There is a need for an automated method to obtain the structure of the fibrosis of the muscle using 3D medical images or data acquired via an acquisition technology in order to provide a basis with which to identify the arrhythmic substrate. This is useful to stratify patients according to the condition of their hearts from cardiac MRI, to decide on their treatment (for example to establish their responsiveness to an implantable defibrillator or to plan catheter ablation procedures).

Cardiac arrhythmias are caused by slow-conducting electrical circuits that use the abnormal structure of the myocardium that results from disease or infarction. The slow conduction of the electrical circuits is responsible for an electrical wave that is out of sync with the main wave responsible for the contraction of the ventricle. The asynchronous wave disrupts the healthy contraction of the myocardium, and this generates arrhythmia.

These electrical circuits join areas of healthy tissue and run through corridors within, see FIG. 1, Border-Zone (BZ) tissue (these corridors will be referred as re-entrant Conducting Channels or CC). In order for the slow wave to propagate and disrupt the main electrical activity, it needs to run through conducting tissue embedded within electrically isolating tissue. This tissue can be either scar core (dead myocytes that no longer conduct), or the wall of the endocardium and epicardium, and/or the mitral valve. The electrical isolation has to fulfill several characteristics in order to be the basis of a wave for a CC:

It needs to run for a minimum distance to allow sufficient time to have passed so that the main electrical wave has passed and the healthy myocytes are excitable again.

It needs a certain topology and morphology with a minimum amount of isolating tissue surrounding the CC. The isolating tissue can be either totally or partially covering the CC.

CCs that are totally covered for a minimum distance are highly likely to contribute to an arrhythmogenic event. However, the ability of partially covered CCs to contribute to arrhythmogenic events depends on several morphological factors, which are analyzed in present invention.

SUMMARY

The present invention describes a method to obtain a measure of the local spatial structure of conducting properties of muscle tissue from medical images or from data acquired by a catheter or another data acquisition technology. This measure is associated with pathological conduction pathways in the tissue, and therefore can be used to help with automatically identifying potential re-entrant conducting channels (CCs) that are the cause of arrhythmia. The method works by analyzing the spatial distribution of tissue properties (obtained by interpreting the output of an acquisition method, e.g., absorption of X-rays, water content or retention of a contrast agent) in the local neighborhoods of several given points and creating output values for each of those points indicating their respective conductive structure properties.

To that end, embodiments of the present invention provide according to an aspect a computer implemented method for calculating values indicative for the local spatial structure of conducting properties of heart muscle tissue, using a continuous region of interest (ROI) where it is considered that there may exist a CC, wherein each point of the ROI being associated with a value of a given spatial distribution having been acquired via an acquisition technology, the method comprising performing, by a processor of a computer system, for each one of a plurality of points (or set of points) within the ROI, the following steps:

a) spanning a plurality of rays within the ROI in multiple 3-D directions by at least using coordinates of a reference coordinate system of each point, providing a structure with a plurality of rays with a given geometry;
b) defining a sequence of sampling points on each ray of said structure;
c) mapping the value of the spatial distribution on each defined sampling point of each ray of the structure;
d) classifying each ray of the structure by assigning to each ray a single value based on the mapped values, the absolute positions within said reference coordinate system of the sampling points, and the positions of the sampling points relative to each ray of the structure, providing an associated ray value; and
e) reducing each structure to a single point value in view of the geometry of the rays and their associated ray value, wherein said single point value (also termed Channelicity in present invention description) being indicative of a local spatial structure of conducting properties of an area of heart muscle tissue.

According to the proposed method, said acquisition technology may comprise an image acquisition technology such as Computed Tomography (CT) or Magnetic Resonance Imaging (MRI), among others, or may comprise a data acquisition technology including a medical instrument measuring voltage, by contact, of the heart muscle tissue, such as a catheter.

In an embodiment, the plurality of points are sampling points on a CC previously detected. Alternatively, the plurality of points are sampling points contained in a part of, or the whole, ROI.

In an embodiment, step a) further comprises using domain-specific geometric information of the heart muscle tissue, said domain-specific geometric information at least including an orientation of the cardiac wall of the heart muscle tissue.

In an embodiment, the ROI consists of a 3D volume enclosed by a topological 2-manifold. In this case, the plurality of rays are straight-line segments from the given initial point to a first point of intersection of the rays with the manifold. In another embodiment, the ROI consists of a triangular surface mesh. In this case, the plurality of rays are straight line segments within the triangles, said segments being joint at the triangular edges by sharing one edge point and having the vertically opposed angles equal.

Preferably, the sequence of sampling points is limited to a given length of the plurality of rays. Besides, the sequence of sampling points is defined according to a set of distances defined for each ray of the plurality of rays, said set of distances comprising a sequence with ascending distance from the given initial point.

According to the proposed method, the cited step e) may be performed by averaging the associated values of each ray using weights derived from the geometry of the rays or, alternatively, by statistically processing relative frequencies of the ray classification.

In a particular embodiment, the spatial distribution comprises different values representing electrical functionality of the heart muscle tissue, wherein a first of said different values, or Healthy, represents tissue with normal electrical functionality; a second of said different values, or Border-Zone, represents tissue with abnormal electrical behavior; and a third of said different values, or Core, represents tissue with no electrical functionality.

According to this particular embodiment, the associated ray value of each ray is provided by traversing the sampling points and their associated values starting from the given initial point and reporting information about the finding of a first value of a given category within the cited Healthy, Border-Zone and Core categories.

Moreover, the associated ray value of each ray can be provided according to the following rules: if the values corresponding to all sampling points of the ray are Border-Zone, then Border-Zone is assigned; otherwise, the value of the closest sampling point whose value isn't Border-Zone, is assigned. The reduced single point value in this embodiment is defined as follows: if there is at least one ray value Healthy, then 0; otherwise, by calculating a core surrounding parameter as weighted relative frequency of core rays or by calculating the single point value from the core surrounding parameter using an affine-linear function and clipping the result at a certain lower and upper threshold.

According to said particular embodiment, the method may further create a volume image of the single point value by assigning to all voxels of the ROI whose value is Border-Zone the reduced value obtained in step e) and by assigning to all other voxels the value 0, and further visualizing the created volume image by means of volume rendering or a marching cubes calculation or using the created volume image for further processing.

Even, according to said particular embodiment, the method may further create sampling points on a given CC centerline such that there are sampling points on every end point and bifurcation and the line segments between sampling points are short enough; calculate the single point value at every one of said created sampling points, interpolated linearly between the latter; and numerically integrate the single point value over the whole trajectory of the CC centerline, providing a centerline's single point value.

In yet another embodiment of the proposed method, a distance to a non-Border-Zone point is recorded, wherein there is no limit of the ray length; and a directionality analysis is performed on the rays by applying a statistical procedure thereof such as a Principal Component Analysis, PCA.

Other embodiments of the invention that are disclosed herein also include software programs to perform the method embodiment steps and operations summarized above and disclosed in detail below. More particularly, a computer program product is one embodiment that has a computer-readable medium including computer program instructions encoded thereon that when executed on at least one processor in a computer system causes the processor to perform the operations indicated herein as embodiments of the invention.

BRIEF DESCRIPTION OF THE DRAWINGS

The previous and other advantages and features will be more fully understood from the following detailed description of embodiments, with reference to the attached figures, which must be considered in an illustrative and non-limiting manner, in which:

FIG. 5a represents the input of the point value reduction (rays with assigned values); FIG. 5b represents the point set used in PCA (central point displaced in ray directions by distances proportional to ray values); and FIG. 5c represents the principal components of the point set from FIG. 5b.

DETAILED DESCRIPTION

Figure 1:
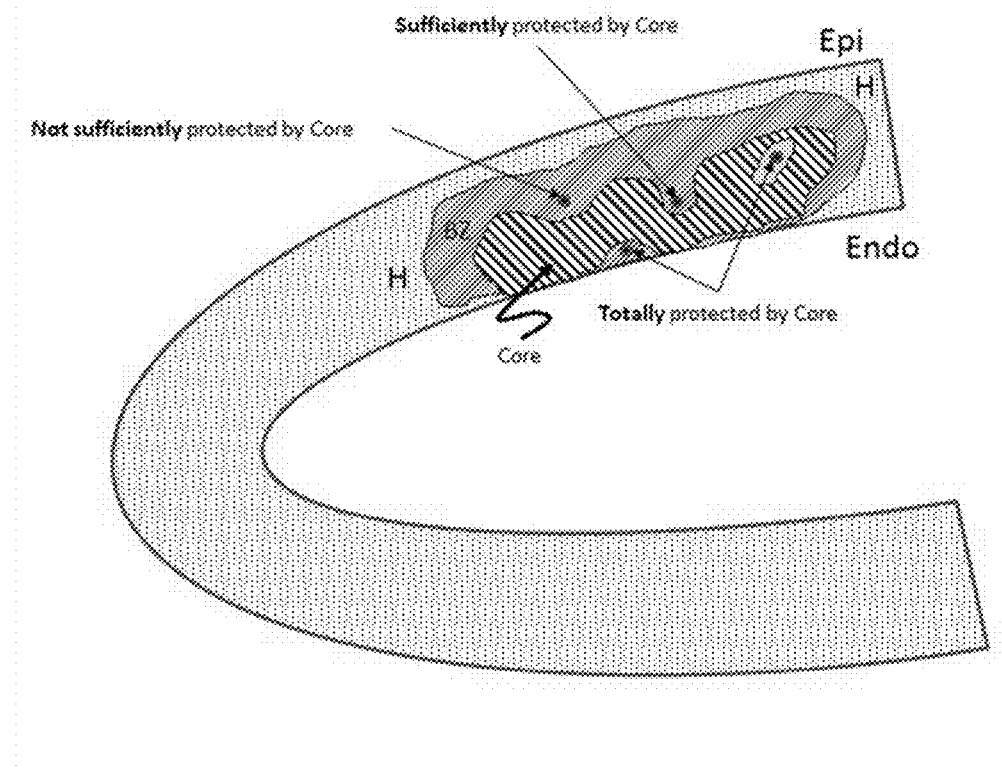
FIG. 1 illustrates the different types of CCs that can be found in heart muscle tissue and characterized by the present invention.
Figure 2:
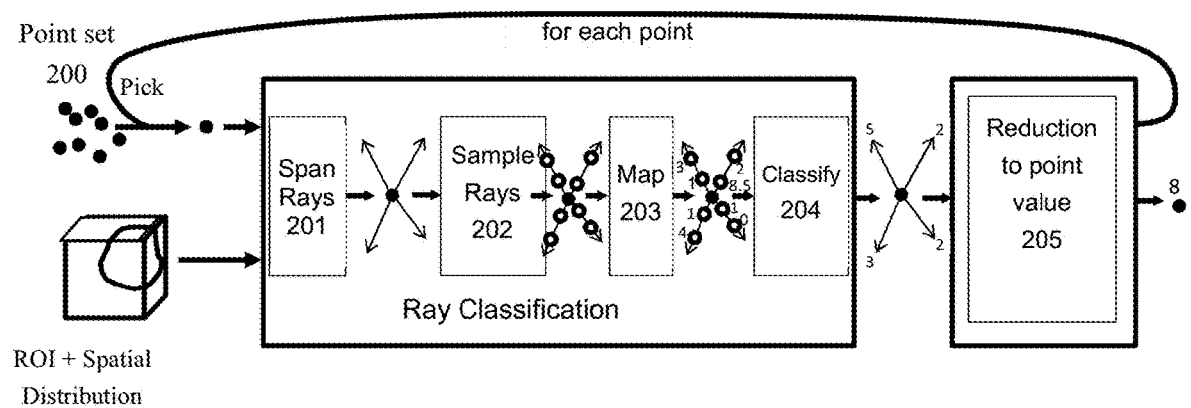
FIG. 2 schematically illustrates a general method workflow with their inputs and outputs for calculating values indicative for the local spatial structure of conducting properties of heart muscle tissue according to the proposed invention.

FIG. 2 shows the main components of the workflow implemented by the proposed invention, with their inputs and outputs, for calculating values indicative for the local spatial structure of conducting properties of heart muscle tissue. The proposed method extracts information about the structure surrounding any of a given finite set of points 200 by processing spatial distribution of a value related to tissue properties in the following way:

For every point of said given set of points 200 whose Channelicity (i.e. a measure of the local spatial structure of conducting properties of muscle tissue) has to be calculated, the method executes the following steps via a processor of a computer system (not illustrated):

1. Ray Classification:
    Span rays 201 starting from the given initial point in multiple 3D directions, providing a structure with a plurality of rays with a given geometry.
    Define 202 a sequence of sampling points on each of the rays of the structure.
    Map 203 the value of the spatial distribution to the sampling points.
    Assign 204 every ray a single value based on the mapped values, the absolute positions of the sampling points and the positions of the sampling points relative to each ray of the structure (distance to ray base), providing an associated ray value.
2. Reduction to point value (205):
    A single value (scalar or vector) is calculated from the ray geometries and their associated ray value.

Following, the different inputs and output of the method and the different components workflow will be detailed:

Inputs and Output

The method needs the following data as input:

A Region of Interest (ROI), which preferably is a subspace of $\mathbb{R}^3$ in which there exists a path of finite length between every pair of points. This mostly rules out very complex geometries like fractals, but also limits the ROIs to path-connected spaces. The latter limitation can be overcome in many real-world cases by running the whole method several times on suitable subsets of the whole ROI and the corresponding subsets of the point set 200. Examples for such ROIs include the myocardium of a full heart or a single heart chamber as well as a two-dimensional surface representation of a heart chamber (ignoring transmural information).

The spatial distributions of acquired information in the ROI, assigning a value to every point of the ROI. This can be a scalar field, vector field, another distribution or combinations of them. In the following, it will be referred to the Cartesian product of the underlying distribution functions as one single "spatial distribution". A typical example for the spatial distribution would be a 3D image from a medical imaging device with trilinear interpolation on the cuboids between the voxel centers.

A finite set of points 200 whose single point value (i.e. the Channelicity) is to be calculated. All points 200 must fall into the ROI.

The output of the method is a single "Channelicity" value for each point of the input point set 200.

Step 201: Ray Spanning

Input:
    Coordinates of one point p of the set or plurality of points 200 whose Channelicity is to be calculated
    (Optional) Domain-specific geometric information Output:
    A finite sequence c of $n_r$ normalized vectors representing ray directions The algorithm implemented by the proposed method spans $n_r$ rays (providing said structure with a particular geometry) by defining their ray directions c as normalized vectors (magnitude 1) tangential to the ROI in the given point p.

Usually a general-purpose algorithm for Sphere Point Picking on the unit sphere (e.g. [1], [2] or [3]) is used to create the direction vectors. These algorithms attempt to create a distribution of the direction vectors on the unit sphere that is uniform as possible.

But depending on the application other algorithms may be used in order to achieve a specific distribution of directions. The algorithm may also take into account the point position p as well as additional domain-specific geometric information, e.g. the orientation of the cardiac wall in order to have a lower density of rays perpendicular to the wall than in the electrophysiologically more relevant tangential directions.

Step 202: Sampling of Ray Trajectories

Input:
    Coordinates of the point p whose Channelicity is to be calculated.
    The sequence c of $n_r$ normalized vectors representing ray directions (output of step 201).

Output:
   One sequence s(i) of $n_s(i)$ sampling points for every ray index i.
   One sequence g(i) of the distances of each of the $n_s(i)$ sampling points from the initial point p for every ray index i.

Ray Trajectory Definition:
   Graphically, a maximal ray from a point p in a direction c(i) is a path starting from p in direction c and continuing as straight as the ROI allows it (locally minimizing distances) infinitely or until it cannot continue straight within the ROI anymore.

Formal Definition:
   A ray from a point p is a continuous function r from a left-closed interval I (starting from 0) to the ROI with r(0)=p and the geodesic property fulfilled for all s in the interior of I. The geodesic property at a point s is fulfilled, if and only if there is a neighborhood V of s such that for all $s_1$ and $s_2$ in V $d_{intrinsic}(r(s_1), r(s_2))=d(s_1, s_2)$ with $d_{intrinsic}$ being the intrinsic metric on the ROI induced by the Euclidian metric on $\mathbb{R}^3$ and d being the Euclidian metric on $\mathbb{R}$.
   A maximal ray from p in direction c(i) is a ray r with r'(0)=c(i) (if the domain contains more than one point) that is maximal according to the following partial of rays: A ray is greater or equal, than a second ray, if and only if its domain is greater or equal and it coincides with the other ray on the intersection of their domains.

Detailed Definition and Interpretation

A path is a continuous function q from an Interval I=[a,b] of $\mathbb{R}$ to the ROI S. A path is called a path between $x_0$ and $x_1$, if and only if q(a)=$x_0$ and q(b)=$x_1$. The length of a path is defined as the supremum of the lengths of all possible rectifications of the path, wherein the length of a rectification is defined as the distance between all subsequent point pairs of the rectification according to the metric used in $\mathbb{R}^3$.

This induces the following intrinsic metric $d_{intrinsic}$ on the ROI: The distance between two points $p_1$ and $p_2$ in the ROI is defined as the infimum of the lengths of all finite paths between $p_1$ and $p_2$. Since all path lengths are non-negative numbers and by requirement of the ROI there exists a path with finite length between all points in ROI, the infimum exists and is always a non-negative real number. It can be shown that the function $d_{intrinsic}$ also fulfills the other requirements for being a metric, which is omitted here.

A ray from p is a continuous function r from a closed or right-open interval I starting from 0 (i.e. it has the form [0, a], or [0, a[ or [0, ∞[ for a $\in \mathbb{R}$) to the ROI with r(0)=p and the geodesic property fulfilled for all s in the interior of I (i.e. ]0, a[ or ]0, ∞[). The geodesic property at a point s is fulfilled, if and only if there is a neighborhood V of s such that $d_{intrinsic}(r(s_1), r(s_2))=d(s_1, s_2)$ for all $s_1$ and $s_2$ in V with d being the Euclidean metric on $\mathbb{R}$. Note that this requirement also implies a natural parameterization (function parameter represents arc length).

A partial order on the set of rays can be defined like this: A ray $r_b$ is greater or equal than a ray $r_a$, if and only if the domain of ray $r_b$ is a non-strict superset of the domain of ray $r_a$ and their values coincide on the intersection of their domains. Graphically, both rays start out with the same trajectory, but $r_b$ may continue further than ray $r_a$. From now on, the method is only interested in rays that are maximal elements according to this order.

A ray in direction c(i) is a ray r which is either differentiable in 0 with r'(0)=c(i) or defined only on the point 0.

For many real-world cases of ROIs there is exactly one maximal ray for each given initial point and direction. However, that unique maximal ray may be of length 0 (if the direction points into a direction in which the ROI doesn't extend), so in cases of more complex ROIs care has to be taken to select ray directions that are compatible with the ROI in the sense that they produce non-trivial rays. For example, if the ROI consists of a 2-manifold, the rays have to be within the tangential plane of the ROI in the ray's initial point.

However, in some pathological ROI sets there might be more than one maximal ray for a given initial point and direction. In applications that allow such ROIs, the proposed method must employ an additional criterion to choose one maximal ray in a deterministic manner.

Examples of Rays in Different ROIs:
   Using the whole $\mathbb{R}^3$ space as ROI, a maximal ray starting from p in a given direction c(i) is simply a straight geometric ray: $\text{Ray}_{p,c(i)}(m)=p+m*c(i)$ for $m \in [0, \infty[$.
   In any 2-dimensional affine-linear subspace of $\mathbb{R}^3$ the maximal rays are either straight geometric rays (if the direction is within the subspace) or single points (if the direction points out of the subspace).

Computational Calculation of Ray Trajectories
3D Volume Enclosed by Topological 2-Manifold:
   In the case of 3D volumes enclosed by topological 2-manifold, like e.g. the myocardium volume enclosed by a closed surface mesh defined by a segmentation process, a ray is a straight-line segment from the given initial point to the first point of intersection s of the ray with the manifold: $\text{Ray}_{p,c(i)}(m)=p+m*c(i)$ for $m \in [0, d(s, p)]$, with d being the Euclidian 3D metric.

Figure 3:
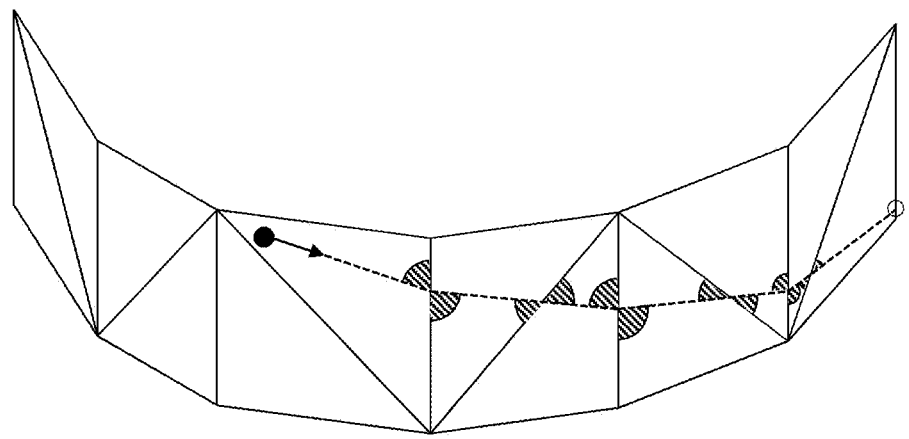
FIG. 3 is a perspective illustration of a ray on a triangular mesh representing a curved strip as a sequence of rectangles being formed by two triangles each, according to an embodiment of the present invention.

Triangular Surface Mesh:
   Maximal rays on triangular surface meshes are one-dimensional polygonal curves. They consist of straight line segments within the triangles. The segments are joint at the triangle edges by sharing one edge point and having the vertically opposed angles (between ray and triangle edge, measured in their respective triangle) equal. The sequence is continued indefinitely until it possibly encounters a simple edge (one that forms part of only one triangle). If such a simple edge is reached by the ray, the ray's intersection with the simple edge is the end point of the ray. Otherwise the ray is of infinite length. FIG. 3 shows an example of such type of ROI. As can be seen in the figure, the equal opposite angles between ray and edge are marked with a crisscross pattern. One can observe that the ray is no longer straight in this case, but follows the curvature of the strip, changing its direction at every transition between rectangles (but not at the edges within rectangles) in order to follow the curvature, but keeping its downward tendency given by the initial ray direction (drawn as arrow). The initial point is marked as a filled circle and the end point at the ray's intersection with a simple edge is marked as an empty circle.

Sampling
   For every ray index i a discrete set of distances is defined, represented as sequence g(i) of ascending distances from the point p.
   The trajectory of the maximal ray $\text{Ray}_{p,c(i)}$ from the given point p in the given direction c(i) is evaluated at each value of g(i):

$$s(i)(j)=\text{Ray}_{p,c(i)}(g(i)(j)) \text{ for each } j$$

Those are the sampling points on the maximal ray defined by the point p and the direction c(i).

Step 203: Mapping
Input:
  The sequences s(i) of $n_s(i)$ sampling points from the previous step 202.
  The spatial distribution representing the tissue properties.
Output:
  One sequence v(i) of values for every ray i, corresponding to the $n_s(i)$ sampling points s(i).
  The input field is evaluated at every one of the $n_s(i)$ sampling points s(i)(j) on every ray i. Depending on the definition of the field, this may include interpolation and/or other mathematical operations. For example, if the continuous field is defined as trilinear interpolation of a 3-D image, in this step the interpolation has to be performed on every one of the sampling points.

Step 204: Ray Values
Input:
  Coordinates of the point p whose Channelicity is to be calculated
  The sequences s(i) of the $n_s(i)$ sampling points from step 2020.
  The sequences g(i) of the $n_s(i)$ distances of the sampling points from the initial point from step 202.
  The sequences v(i) of the $n_s(i)$ mapped values from 203.
Output:
  A sequence w of the $n_r$ ray classifications.
  The mapped values of every sampling point and the location of the sampling points, both in absolute coordinates and relative to the point p, are used to produce a single classification for every ray.
  Examples of this process include traversing the sampling points and their associated values starting from the ray origin and reporting information about the finding of the first value of a given category (for example as specified in following sections, Ray Classification: Contact with non-BZ tissue and Core Distance).

Step 205: Reduction to Point Value
Input:
  Coordinates of the point p whose Channelicity is to be calculated.
  The sequence c of $n_r$ normalized vectors representing ray directions (output of 201).
  The sequence w of ray classifications for the $n_r$ rays from 204.
  (Optional) Domain-specific geometric information.
Output:
  One single point classification value.
  The classifications of all the rays as well as geometric information about the rays and (optionally) addition domain-specific geometric information are used to produce a single classification for the input point p.
  For example, this step can consist of averaging the ray classification values, possibly using weights derived from the geometric information (e.g. giving rays running tangential to the cardiac wall a higher weight than transmural rays due to anisotropic electrical properties). Another example is statistical processing of the relative frequencies of ray classifications, again possibly using weights derived from the geometric information.

Local Channelicity

One particular example embodiment of the proposed method is the calculation of a measure of how enclosed within isolating tissue a point is.

The spatial distribution input is a ternary scalar field containing the values H (Healthy), BZ (Border-Zone) and K (Core). Those values represent the electrical functionality of the myocardium tissue. Zones of "healthy" tissue represent tissue that works mostly normal, "border-zone" represents tissue with abnormal electrical behavior (mostly slowed electrical propagation) and "core" represents tissue with no active electrical functionality (only passive conduction, if any).

This field is usually derived from a medical image with injected contrast that shows the tissue functionality as gray value, for example gadolinium-enhanced magnetic resonance images. A simple way to obtain the spatial distribution of the functionality from such an image is to apply trilinear interpolation to the image and classify the interpolated values within the myocardium by using two thresholds. Values below the lower threshold are classified as H, values between the lower and the upper threshold are classified as BZ and values above the upper threshold are classified as K.

Ray Classification: Contact with Non-BZ Tissue

The rays of step 201 are defined as a fixed number of rays (typically 30, however other amounts of rays are also possible) that are distributed as uniformly as possible using a Sphere Point Picking algorithm.

The sampling points of step 202 are distributed equidistantly (e.g. at distance of half the voxel spacing) from the ray base to a fixed length (typically 3.5 mm).

The ray value of step 204 can be assigned according to the following rules:
  If the values corresponding to all sampling points are BZ, then BZ.
  Otherwise, the value of the closest sampling point whose value isn't BZ.

If there are less sampling points than expected (because the ray touches the border of the ROI, e.g. rays 7 and 8 in the example below), process the ray as if there was an additional sampling point with the value K at the end, in order to account for the fact that the space outside of the ROI is considered non-conducting.

Example 1

| | Sampling Point | | | | | | | | Ray value |
|---|---|---|---|---|---|---|---|---|---|
| | 1 | 2 | 3 | 4 | 5 | 6 | 7 | | |
| Ray 1 | BZ | BZ | BZ | BZ | BZ | BZ | BZ | → | BZ |
| Ray 2 | BZ | BZ | BZ | BZ | BZ | BZ | H | → | H |
| Ray 3 | BZ | BZ | BZ | BZ | BZ | BZ | K | → | K |
| Ray 4 | BZ | BZ | BZ | H | H | BZ | K | → | H |
| Ray 5 | K | K | BZ | BZ | K | K | BZ | → | K |
| Ray 6 | BZ | BZ | K | K | BZ | BZ | H | → | K |
| Ray 7 | BZ | BZ | BZ | BZ | BZ | — | — | → | K |
| Ray 8 | BZ | BZ | H | BZ | BZ | — | — | → | H |

Point Value Reduction: Core Surrounding

The point value (called "Local Channelicity" in this particular exemplary embodiment) of the reduction (step 205) can be defined as follows:
  If there is at least one ray value H, then 0.
  Otherwise, the following procedure is applied:
    Calculate the "Core Surrounding" as weighted relative frequency of Core rays. The weights are a function that varies affine-linearly with the angle between the ray and the cardiac wall's tangential plane.
    Calculate the "Local Channelicity" using an affine-linear function defined by the mappings [a→0] and [b→1] (with a typically being 15% and b being 40%) and cutting off values below 0% and above 100%.

Example 2

| Healthy Rays | Border-Zone Rays | Core Rays | Core Surrounding | Local Channelicity |
|---|---|---|---|---|
| 0 | 19 | 1 | 5% | 0% |
| 0 | 17 | 3 | 15% | 0% |
| 0 | 12 | 8 | 40% | 100% |
| 0 | 8 | 12 | 60% | 100% |
| 0 | 15 | 5 | 25% | 40% |
| 1 | 14 | 5 | 25% | 0% |

Application: Volume Channelicity

In order to obtain a Volume Channelicity image, a volume image is created according to the following rules: All voxels, whose ternary spatial distribution value is BZ, are assigned the value calculated by the algorithm presented in the previous section 'Point Value Reduction: Core Surrounding'. All other voxels are assigned the value 0. The resulting distribution of tissue with possibly arrhythmogenic properties can be visualized using volume rendering or surface rendering after performing a marching cubes calculation, or used for further processing in the detection of CCs.

Application: Filter Channels Detected in Layers

The Local Channelicity also allows filtering out false positives of CCs detected by an external CC detection algorithm. This can be done by applying a threshold filter to a Channelicity value of the CC. The CC's Channelicity may be calculated as follows.

A centerline of a CC is sampled with a high enough resolution, having sampling points on every bifurcation (if there are branches) and at every end point. This is done by putting initial sampling points on every end point and bifurcation and iteratively subdividing the linear segments between sampling points until all segments have a length below a given threshold. The Local Channelicity is calculated at every sampling point and interpolated linearly between sampling points. The Local Channelicity is then integrated numerically over the whole trajectory of the CC's centerline. The resulting value is the centerline's Channelicity.

Since the Local Channelicity is between 0% (=0) and 100% (=1), a centerline's Channelicity can be between 0, when the Local Channelicity is 0% everywhere, and the length of the centerline's trajectory, if the Local Channelicity is 100% everywhere.

For example, a centerline of 10 mm length and a constant Local Channelicity of 0% (no arrhythmogenicity anywhere) have a Channelicity of 0 mm. A centerline of 10 mm length and a constant Local Channelicity of 100% (completely arrhythmogenic everywhere) have a Channelicity of 10 mm. A centerline of 10 mm length with a constant Local Channelicity of 50% everywhere has a Channelicity of 5 mm. A centerline of 10 mm length with a Local Channelicity of 100% during half of its trajectory and 0% during the other half has a Channelicity of 5 mm, too.

Method Instances Using Propagation Range

This section describes another particular example embodiment of the proposed method. While the method described in the 'Ray Classification: Contact with non-BZ tissue' section performs only a qualitative evaluation of the conductive properties in each direction, a quantitative evaluation of the excitation wave's "range" (e.g. until it touches a non-conductive obstacle, or the distance a stimulus can travel in that direction within a certain time limit) is also possible. The obtained quantitative information can help to improve the point reduction's robustness and level of detail (see following section 'Continuous Core Surrounding') or even enable new point reduction techniques that use the quantitative information for directionality analyses (section 'Directionality Analysis').

Ray Classification: Range

Figure 4:
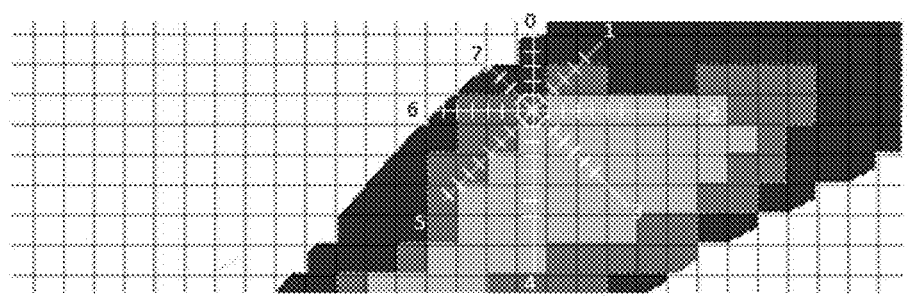
FIG. 4 illustrates an example of the results obtained by the core distance process, according to an embodiment of the present invention. The figure illustrates rays in several directions probing for Core presence and recording its distance (Ray 0: 1, Ray 1: 5, Ray 2: ∞, Ray 3: ∞, Ray 4: ∞, Ray 5: 10, Ray 6: 5, Ray 7: 2).
Figure 5:
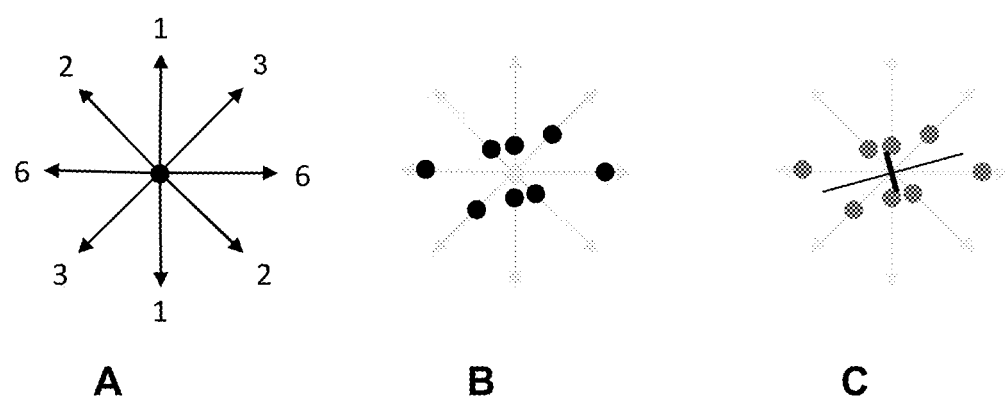
FIG. 5 illustrates an example of the intermediate results obtained from the directionality analysis process, according to an embodiment of the present invention.

Core Distance:

This "Ray Classification" method is similar to the one introduced in the 'Ray Classification: Contact with non-BZ tissue' section in that it traverses every ray from the initial point until it discovers anything different from BZ. However, instead of just recording the tissue type discovered, it records the distance to the non-BZ point, if K is found, or infinity, if H is found. That can be interpreted as the distance to the closest K tissue that can be reached in the particular direction without having to pass through H first. In contrast to said previous method, there is no fixed limit of the ray length: Sampling points are placed on the ray equidistant sections until the ray leaves the ROI. FIG. 4 shows an example using this method.

Like in the 'Ray Classification: Contact with non-BZ tissue' section, an additional implicit sampling point with the value K is assumed at the end of the ray.

Example 3

| BZ | BZ | BZ | BZ | BZ | BZ | H | → | ∞ |
| BZ | BZ | BZ | BZ | BZ | BZ | K | → | 6 |
| BZ | BZ | BZ | H | H | BZ | K | → | ∞ |
| K | K | BZ | BZ | K | K | BZ | → | 0 |
| BZ | BZ | K | K | BZ | BZ | H | → | 2 |

Intensity-Based Range (Simulation):

This "Ray Classification" method determines for every ray the distance that a stimulus can travel in that direction within a fixed timeframe. It does so by performing a one-dimensional Eikonal-type simulation, with the propagation velocity at every sampling point being determined by the value of the input scalar field at that point and inverse velocities being interpolated in between.

The simulation starts at time 0, for which the stimulus wavefront is at position 0 from the ray origin. It proceeds until a fixed simulation time $t_{end}$ is reached and returns the distance that the stimulus has traveled in the duration.

For every segment between the sampling points s(i)(j) and s(i)(j+1) of geodesic ray segment length x=g(i)(j+1)−g(i)(i) the quadratic relationship between position and local activation time of the stimulus within the segment is calculated by calculating the stimulus velocities $v_a$ and $v_b$ at the two end points s(i)(j) and s(i)(j+1), respectively, using the pixel intensities from the mapping step and assuming an affine-linear distribution of the inverse velocities (time per distance) in between. If the total time of the segment, defined as sum of times of all segments up to the current one, is lower than the given simulation time $t_{end}$, then the simulation proceeds to the next segment. Otherwise the quadratic position-time relationship is used to determine the exact distance, at which the stimulus is a time $t_{end}$, end the value is returned as result.

The exact relationship between pixel intensity and stimulus propagation velocity depends on the chosen model, but is usually a monotonically decreasing function approximating 0 when the pixel intensity of dense scar is reached.

Reduction to Point Value
Continuous Core Surrounding:

The calculation of the Core Surrounding in 'Point Value Reduction: Core Surrounding' section takes into account only the discrete classification of rays (Core vs. Non-Core, blocked vs. conducting). However, with the additional range information, obtained from the methods in 'Ray Classification: Range' section a similar calculation can be performed using the range as indicator of how well the tissue conducts a stimulus locally in a given direction. Instead of using a weighted relative frequency of Core rays, which would be equivalent to a weighted average of the indicator function of Core rays (1 for Core rays, 0 for other rays), a weighted average of a continuous value can be used. For this purpose, the range obtained from the Ray Classification is transformed by a continuous monotonically decreasing function.

Directionality Analysis

The ray ranges calculated in 'Ray Classification: Range' section can be used to perform a directionality analysis that tells how strongly the excitation wave is guided in one particular direction and which direction that is. Thereto, in an embodiment, Principal Component Analysis (PCA) or similar techniques can be applied to a point set that is calculated in the following manner: For every ray the method creates a point that is displaced from the central point in ray direction by a distance proportional to the ray range.

The Principal Components (PC) produced by the PCA are ordered by their magnitude. The direction of the largest PC is used as direction for the output vector. The ratio between the largest PC and the second largest PC is used as magnitude for the output vector.

The proposed invention can be implemented by means of software elements, hardware elements, firmware elements, or any suitable combination of them. If implemented in software, the functions may be stored on or encoded as one or more instructions or code on a computer-readable medium.

Computer-readable media include computer storage media. Storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. Any processor and the storage medium may reside in an ASIC. The ASIC may reside in a user terminal. In the alternative, the processor and the storage medium may reside as discrete components in a user terminal.

As used herein, computer program products comprising computer-readable media including all forms of computer-readable medium except, to the extent that such media is deemed to be non-statutory, transitory propagating signals.

It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The scope of the present invention is defined in the following set of claims.

The invention claimed is:

1. A computer implemented method for calculating values indicative for the local spatial structure of conducting properties of heart muscle tissue, using a continuous region of interest (ROI) where it is considered that there may exist a conducting channel (CC), wherein each point of the ROI being associated with a value of a given spatial distribution having been acquired via an acquisition technology, the method comprising performing, by a processor of a computer system, for each one of a plurality of points within the ROI, the following steps:
   a) spanning a plurality of rays within the ROI in multiple 3-D directions by at least using coordinates of a reference coordinate system of each point, providing a structure with a plurality of rays with a given geometry;
   b) defining a sequence of sampling points on each ray of said structure;
   c) mapping the value of the spatial distribution on each defined sampling point of each ray of the structure;
   d) classifying each ray of the structure by assigning to each ray a single value based on:
      the mapped values,
      the absolute positions within said reference coordinate system of the sampling points, and
      the positions of the sampling points relative to each ray of the structure, providing an associated ray value; and
   e) reducing each structure to a single point value in view of the geometry of the rays and their associated ray value, wherein said single point value being indicative of a local spatial structure of conducting properties of an area of heart muscle tissue.

2. The method of claim 1, wherein the plurality of points being sampling points on a CC previously detected or sampling points being contained in a part of or the whole ROI.

3. The method of claim 1, wherein said step a) further comprises using domain-specific geometric information of the heart muscle tissue, said domain-specific geometric information at least including an orientation of the cardiac wall of the heart muscle tissue.

4. The method of claim 1, wherein:
   said acquisition technology comprising an image acquisition technology comprising at least Computed Tomography (CT) or Magnetic Resonance Imaging (MRI); or
   said acquisition technology comprising a data acquisition technology including a medical instrument measuring voltage, by contact, of the heart muscle tissue.

5. The method of claim 1, wherein the ROI consists of:
   a 3D volume enclosed by a topological 2-manifold, the plurality of rays being straight-line segments from the given initial point to a first portion of intersection of the rays with the manifold; or
   a triangular surface mesh, the plurality of rays being straight line segments within the triangles, said segments being joint at the triangular edges by sharing one edge point and having the vertically opposed angles equal.

6. The method of claim 1, wherein the sequence of sampling points being limited to a given length of the plurality of rays.

7. The method of claim 1, wherein the sequence of sampling points being defined according to a set of distances defined for each ray of the plurality of rays, said set of distances comprising a sequence with ascending distance from the given initial point.

8. The method of claim 6, wherein the sequence of sampling points being further defined according to a set of distances defined for each ray of the plurality of rays, said set of distances comprising a sequence with ascending distance from the given initial point.

9. The method of claim 4, wherein said spatial distribution comprises different values representing electrical functionality of the heart muscle tissue, wherein a first of said different values, or Healthy, represents tissue with normal electrical functionality; a second of said different values, or Border-Zone, represents tissue with abnormal electrical behavior; and a third of said different values, or Core, represents tissue with no electrical functionality.

10. The method of claim 9, wherein the associated ray value of each ray being provided by traversing the sampling points and their associated values starting from the given initial point, and reporting information about the finding of a first value of a given category within the cited Healthy, Border-Zone and Core categories.

11. The method of claim 10, wherein the associated ray value of each ray being provided according to the following rules:
if the values corresponding to all sampling points of the ray are Border-Zone, then Border-Zone is assigned;
otherwise, the value of the closest sampling point whose value isn't Border-Zone, is assigned.

12. The method of claim 11, wherein the reduced single point value being defined according to:
if there is at least one ray value Healthy, then 0;
otherwise, by:
calculating a core surrounding parameter as weighted relative frequency of core rays; and
calculating the single point value from the core surrounding parameter using an affine-linear function and clipping the result at a certain lower and upper threshold.

13. The method of claim 1, wherein step e) being performed by averaging the associated values of each ray using weights derived from the geometry of the rays or by statistically processing relative frequencies of the ray classification.

14. The method of claim 9, further comprising:
creating a volume image of the single point value by assigning to all voxels of the ROI whose value is Border-Zone the reduced value obtained in step e) and by assigning to all other voxels the value 0; and
further performing a marching cubes calculation for visualizing the created volume image or using the created volume image for further processing.

15. The method of claim 9, further comprising:
creating sampling points on a given CC centerline such that there are sampling points on every end point and bifurcation and the line segments between sampling points are short enough; and
calculating the single point value at every one of said created sampling points, interpolated linearly between the latter; and
numerically integrating the single point value over the whole trajectory of the CC centerline, providing a centerline's single point value.

16. The method of claim 11, further comprising:
recording a distance to a non-Border-Zone point, wherein there is no limit of the ray length; and
performing a directionality analysis on the rays by applying a statistical procedure thereof, the statistical procedure including a Principal Component Analysis (PCA).

17. A non-transitory computer readable medium including code instructions that, when executed in a computer, implement a method for calculating values indicative for the local spatial structure of conducting properties of heart muscle tissue, using a continuous region of interest (ROI) where it is considered that there may exist a conducting channel (CC), wherein each point of the ROI being associated with a value of a given spatial distribution having been acquired via an acquisition technology, the method comprising:
a) spanning a plurality of rays within the ROI in multiple 3-D directions by at least using coordinates of a reference coordinate system of each point, providing a structure with a plurality of rays with a given geometry;
b) defining a sequence of sampling points on each ray of said structure;
c) mapping the value of the spatial distribution on each defined sampling point of each ray of the structure;
d) classifying each ray of the structure by assigning to each ray a single value based on:
the mapped values,
the absolute positions within said reference coordinate system of the sampling points, and
the positions of the sampling points relative to each ray of the structure.

* * * * *